United States Patent
Ha

(10) Patent No.: US 12,189,187 B2
(45) Date of Patent: Jan. 7, 2025

(54) OPTICAL ROTARY JUNCTION MODULE FOR OCT SYSTEM

(71) Applicant: RAYWATT Inc., Seoul (KR)

(72) Inventor: Jin Yong Ha, Seoul (KR)

(73) Assignee: RAYWATT Inc., Seoul (KR)

( * ) Notice: Subject to any disclaimer, the term of this patent is extended or adjusted under 35 U.S.C. 154(b) by 111 days.

(21) Appl. No.: 17/779,740

(22) PCT Filed: Nov. 26, 2019

(86) PCT No.: PCT/KR2019/016392
§ 371 (c)(1),
(2) Date: May 25, 2022

(87) PCT Pub. No.: WO2021/107175
PCT Pub. Date: Jun. 3, 2021

(65) Prior Publication Data
US 2023/0003944 A1    Jan. 5, 2023

(30) Foreign Application Priority Data

Nov. 26, 2019 (KR) .................. 10-2019-0153334

(51) Int. Cl.
*G02B 6/36*     (2006.01)
*A61B 1/00*     (2006.01)
(Continued)

(52) U.S. Cl.
CPC ........ *G02B 6/3604* (2013.01); *A61B 1/00126* (2013.01); *A61B 1/07* (2013.01); *A61B 1/3137* (2013.01); *A61B 5/0066* (2013.01)

(58) Field of Classification Search
CPC .. G02B 6/3604; A61B 1/00126; A61B 1/3137
See application file for complete search history.

(56) References Cited

U.S. PATENT DOCUMENTS 6,749,344 B2   6/2004 Hamm et al.
2012/0069348 A1*  3/2012 Jono .............. G02B 6/382
                                                    356/479

FOREIGN PATENT DOCUMENTS

JP      3557519 B2      8/2004
JP      2013-511372 A   4/2013
(Continued)

OTHER PUBLICATIONS

English translation of WO2019221335A1 (Year: 2019).*

*Primary Examiner* — Sung H Pak
(74) *Attorney, Agent, or Firm* — Bridgeway IP Law Group, PLLC; Sang Ho Lee; Hyun Woo Shin

(57) ABSTRACT

An optical rotary junction module for an OCT system according to the present invention includes an OCT connection part having a screw thread formed on an outer peripheral surface thereof, the OCT connection part being connected to an OCT system configured to produce light, a connecting/fixing part having a screw thread formed on an inner peripheral surface thereof and screw-coupled to and engaging with the screw thread formed on the outer peripheral surface of the OCT connection part, a first housing having a screw thread formed on an inner peripheral surface of one end thereof and a screw thread formed on an inner peripheral surface of the other end thereof, the first housing having one end screw-coupled to the connecting/fixing part, a second housing screw-coupled to the screw thread formed on the inner peripheral surface of the other end of the first housing, a hollow motor inserted into the second housing and configured to generate rotational power, and an adapter configured to be coupled to an imaging catheter configured to be inserted into a blood vessel of a human body and transmit light received from the OCT system. The optical rotary junction module has the effects of reducing noise generated during high-speed rotation, and preventing failure (Continued)

caused by abrasion or the like. Moreover, the module may be structurally simplified and reduced in size, and the product cost per unit thereof may be lowered by minimizing the components.

8 Claims, 8 Drawing Sheets

(51) Int. Cl.
*A61B 1/07* (2006.01)
*A61B 1/313* (2006.01)
*A61B 5/00* (2006.01)

(56) References Cited

FOREIGN PATENT DOCUMENTS

| | | |
|---|---|---|
| JP | 2015-006326 A | 1/2015 |
| KR | 10-2018-0138378 A | 12/2018 |
| KR | 10-2019-0130425 A | 11/2019 |
| WO | WO-2019221335 A1 * | 11/2019 ........... A61B 5/0059 |

* cited by examiner

OPTICAL ROTARY JUNCTION MODULE FOR OCT SYSTEM

TECHNICAL FIELD

The present invention relates to an optical rotary junction module for an OCT system, and more particularly, to an optical rotary junction module for an OCT system, in which a coupler for inhibiting tolerance between inner components of a rotary junction module between an OCT system and an imaging catheter is removed, and a joint end capable of performing optical coupling in a free space is implemented, such that tolerance caused by the assembling of the respective components of the rotary junction module may be reduced, and torque of a hollow motor may be transmitted to the imaging catheter without a loss.

BACKGROUND ART

In general, optical coherence tomography (OCT) is used for vascular diseases and provides spatial resolution for shaping an internal structure of a blood vessel or the like of a human body.

The optical coherence tomography may use a laser using chromium in order to produce two types of infrared rays and emit light (light energy) from the laser through a catheter (e.g., a urinary catheter) inserted into a human body so that the light is reflected by a surface of a body organ which is a target.

Further, the light reflected by the surface of the body organ returns along the catheter, and the returning light interferes with separate light. In this case, on the basis of the interaction between the two types of light, it is possible to obtain various types of optical information on positions of photons and how the reflection is performed.

To obtain cardiovascular OCT images, a catheter is positioned in a cardiac blood vessel (with a diameter of 3 to 5 mm) to be evaluated through a femoral artery and an aorta and then captures images of the cardiac blood vessel while being rotated at 100 revolutions per second and pulled back at a speed of 20 mm/s (i.e., 100 frames of the cross-sectional images of the blood vessel are played at an interval of 0.2 mm/s).

In this case, a rotary junction needs to be implemented to rotate and pull the catheter, and an optical rotational device needs to be implemented to connect the catheter and an OCT system and rotate the catheter. It is necessary to minimize an optical coupling loss during a process of aligning a rotating optical system and an adjusted optical system.

However, the rotary junction in the related art is configured by a rotary joint, a shaft coupler, a hollow motor, a shaft coupler, and an adapter component and implemented by being inserted into a module mount with longitudinal axis tolerance minimized by lathe machining.

However, there is a problem in that noise occurs during a high-speed rotation when a coupler, which is a connection part between a fiber optic rotary joint and a shaft, is coupled. Further, there is also a problem in that a commercially available joint is not suitable for a high-speed rotation because of limited performance of the joint, and a corresponding part of the joint is broken down because of abrasion or the like.

DISCLOSURE

Technical Problem

The present invention has been made in an effort to solve the above-mentioned problems, and an object of the present invention is to provide an optical rotary junction module for an OCT system, in which a coupler for inhibiting tolerance between inner components of a rotary junction module between an OCT system and an imaging catheter is removed, and a joint end capable of performing optical coupling in a free space is implemented, such that tolerance caused by the assembling of the respective components of the rotary junction module may be reduced, and torque of a hollow motor may be transmitted to the imaging catheter without a loss.

Technical Solution

To achieve the above-mentioned object, an optical rotary junction module for an OCT system according to the present invention includes: an OCT connection part having a screw thread formed on an outer peripheral surface thereof, the OCT connection part being connected to an OCT system configured to produce light; a connecting/fixing part having a screw thread formed on an inner peripheral surface thereof and screw-coupled to and engaging with the screw thread formed on the outer peripheral surface of the OCT connection part; a first housing having a screw thread formed on an inner peripheral surface of one end thereof and a screw thread formed on an inner peripheral surface of the other end thereof, the first housing having one end screw-coupled to the connecting/fixing part; a second housing screw-coupled to the screw thread formed on the inner peripheral surface of the other end of the first housing; a hollow motor inserted into the second housing and configured to generate rotational power; and an adapter configured to be coupled to an imaging catheter configured to be inserted into a blood vessel of a human body and transmit light received from the OCT system.

The optical rotary junction module according to the present invention for achieving the above-mentioned object may further include: first and second alignment parts provided in the connecting/fixing part and configured to align an optical fiber configured to transmit the light; and a third alignment part disposed between the hollow motor and the adapter.

In the optical rotary junction module according to the present invention for achieving the above-mentioned object, the first alignment part may include: a first ferrule fixing unit having a screw thread formed on a part of an inner peripheral surface thereof and coupled to a stepped portion of the OCT connection part; a first ferrule having a hollow portion so that the optical fiber penetrates the hollow portion, the first ferrule being inserted into and fixed to the first ferrule fixing unit; and a first spring interposed between the first ferrule and an interior of the stepped portion.

In the optical rotary junction module according to the present invention for achieving the above-mentioned object, the second alignment part may include: a first hollow motor connection unit connected to a rotary shaft of one side of the hollow motor; a second ferrule fixing unit having a screw thread formed on an inner peripheral surface thereof and coupled to a screw thread formed on an outer peripheral surface of the first hollow motor connection unit; a second ferrule having a hollow portion so that the optical fiber having passed through the first alignment part penetrates the hollow portion, the second ferrule being inserted into and fixed to the second ferrule fixing unit; and a second spring interposed between the second ferrule and an interior of the first hollow motor connection unit.

In the optical rotary junction module according to the present invention for achieving the above-mentioned object, the third alignment part may include: a second hollow motor connection unit connected to a rotary shaft of the other side of the hollow motor; a third ferrule fixing unit having a screw thread formed on an inner peripheral surface thereof and coupled to a screw thread formed on an outer peripheral surface of the second hollow motor connection unit; a third ferrule having a hollow portion so that the optical fiber having passed through the hollow motor penetrates the hollow portion, the third ferrule being inserted into and fixed to the third ferrule fixing unit; and a third spring interposed between the second ferrule and an interior of the second hollow motor connection unit.

In the optical rotary junction module according to the present invention for achieving the above-mentioned object, the third alignment part may include: a second hollow motor connection unit connected to a rotary shaft of the other side of the hollow motor; a third ferrule having a hollow portion so that the optical fiber having passed through the hollow motor penetrates the hollow portion, the third ferrule being partially inserted into the second hollow motor connection unit; a T-shaped adapter configured such that the second hollow motor connection unit and the third ferrule are inserted into and fixed to the T-shaped adapter; and an SC adapter coupled to the T-shaped adapter and having a hollow portion penetrated by the adapter.

As another embodiment, an optical rotary junction module for an OCT system according to the present invention includes: an OCT connection part having a screw thread formed on an outer peripheral surface thereof, the OCT connection part being connected to an OCT system configured to produce light; a connecting/fixing part having a screw thread formed on an inner peripheral surface thereof and screw-coupled to and engaging with the screw thread formed on the outer peripheral surface of the OCT connection part; first and second alignment parts provided in the connecting/fixing part and configured to align an optical fiber configured to transmit the light; a first housing having a screw thread formed on an inner peripheral surface of one end thereof and a screw thread formed on an inner peripheral surface of the other end thereof, the first housing having one end screw-coupled to the connecting/fixing part; a second housing screw-coupled to the screw thread formed on the inner peripheral surface of the other end of the first housing; a hollow motor inserted into the second housing and configured to generate rotational power; an adapter configured to be coupled to an imaging catheter configured to be inserted into a blood vessel of a human body and transmit light received from the OCT system; and a third alignment part disposed between the hollow motor and the adapter.

In the optical rotary junction module according to the present invention for achieving the above-mentioned object, the first alignment part may include a first ferrule having a hollow penetrated by the optical fiber, and the first ferrule has one end having a stepped structure and is inserted into and coupled to a hollow portion of the OCT connection part having a structure corresponding to the first ferrule.

In the optical rotary junction module according to the present invention for achieving the above-mentioned object, the second alignment part may include a second ferrule having a hollow portion so that the optical fiber having passed through the first alignment part penetrates the hollow portion, and the second ferrule has one end having a stepped structure and is inserted into and coupled directly to a shaft of one side of the hollow motor having a structure corresponding to the second ferrule.

In the optical rotary junction module according to the present invention for achieving the above-mentioned object, the third alignment part may include a third ferrule having a hollow portion so that the optical fiber having passed through the hollow motor penetrates the hollow portion, and the third ferrule is inserted into and fixed directly to a shaft of the other side of the hollow motor.

Advantageous Effects

According to the optical rotary junction module for an OCT system according to the present invention, the coupler for inhibiting tolerance between inner components of the rotary junction module between the OCT system and the imaging catheter is removed. Therefore, it is possible to reduce noise occurring during a high-speed rotation and prevent a breakdown caused by abrasion or the like.

In addition, according to the optical rotary junction module for an OCT system according to the present invention, the coupler for inhibiting tolerance between inner components of the rotary junction module between the OCT system and the imaging catheter is removed. Therefore, it is possible to simplify the structure, reduce the size, minimize the configuration, and reduce the manufacturing cost.

BEST MODE

Figure 1:
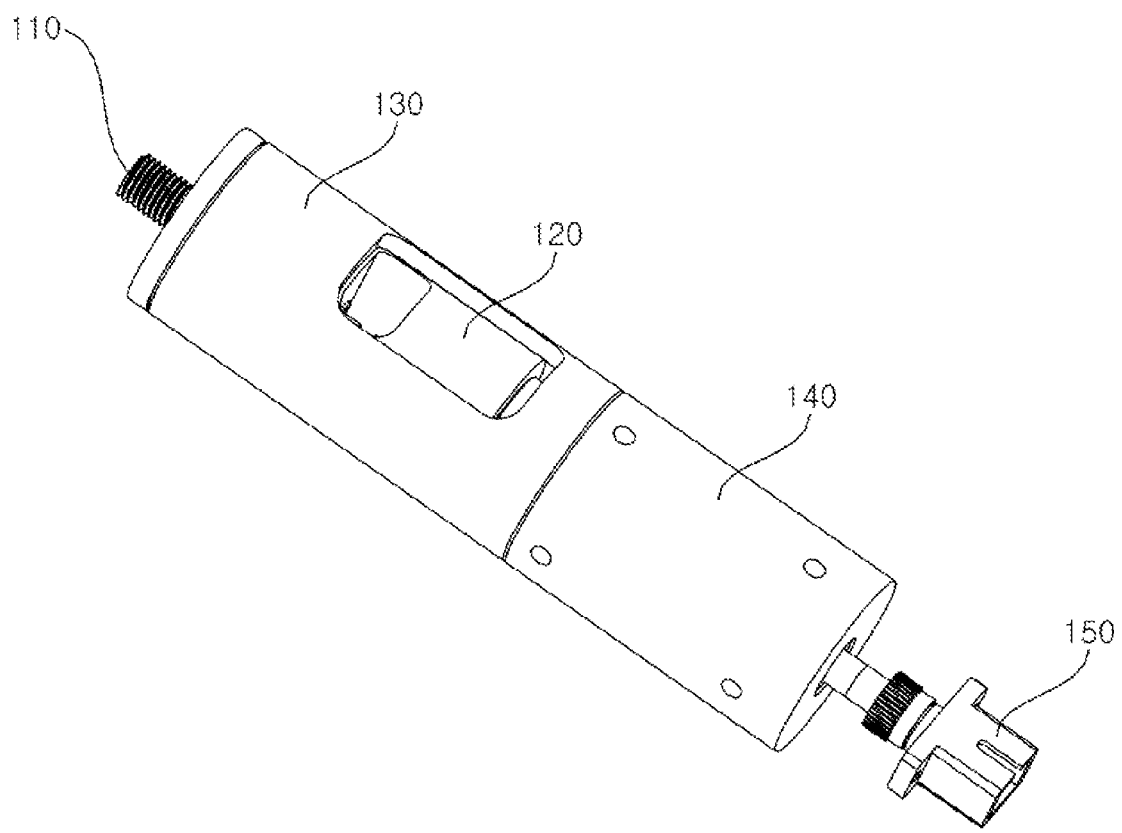
FIG. 1 is a perspective view of an optical rotary junction module for an OCT system according to a first embodiment of the present invention.

The present invention may be variously modified and may have various embodiments, and particular embodiments illustrated in the drawings will be described in detail below. However, the description of the exemplary embodiments is not intended to limit the present invention to the particular exemplary embodiments, but it should be understood that the present invention is to cover all modifications, equivalents and alternatives falling within the spirit and technical scope of the present invention. In the description of the drawings, similar reference numerals are used for similar constituent elements.

The terms such as "first," "second," "A," "B," and other numerical terms may be used herein only to describe various elements, but these elements should not be limited by these terms. These terms are used only to distinguish one constituent element from another constituent element. For example, a first component may be named a second component, and similarly, the second component may also be named the first component, without departing from the scope of the present invention. The term "and/or" includes any and all combinations of a plurality of the related and listed items.

When one constituent element is described as being "coupled" or "connected" to another constituent element, it should be understood that one constituent element can be coupled or connected directly to another constituent element, and an intervening constituent element can also be present between the constituent elements. When one constituent element is described as being "coupled directly to" or "connected directly to" another constituent element, it should be understood that no intervening constituent element is present between the constituent elements.

The terminology used herein is used for the purpose of describing particular embodiments only and is not intended to limit the present invention. Singular expressions include plural expressions unless clearly described as different meanings in the context. The terms "comprises," "comprising," "includes," "including," "containing," "has," "having" or other variations thereof are inclusive and therefore specify the presence of stated features, integers, steps, operations, elements, and/or components, but do not preclude the presence or addition of one or more other features, integers, steps, operations, elements, components, and/or groups thereof.

Unless otherwise defined, all terms used herein, including technical or scientific terms, have the same meaning as commonly understood by those skilled in the art to which the present invention pertains. The terms such as those defined in a commonly used dictionary should be interpreted as having meanings consistent with meanings in the context of related technologies and should not be interpreted as ideal or excessively formal meanings unless explicitly defined in the present application.

Throughout the specification and claims, unless explicitly described to the contrary, the word "comprise" or "include" and variations, such as "comprises", "comprising", "includes" or "including", will be understood to imply the inclusion of stated constituent elements, not the exclusion of any other constituent elements.

Hereinafter, exemplary embodiments according to the present invention will be described in detail with reference to the accompanying drawings.

First, periphery components coupled to a rotary junction module 100 according to the present invention will be briefly described. An OCT system connected to one end of the rotary junction module 100 includes a laser part, an interferometer and detection part), and a data acquisition part.

To capture images of a blood vessel wall of an object, an imaging catheter connected to the other end of the rotary junction module may emit light, which is transmitted from the OCT system, to tissue of the blood vessel wall, receive the light scattered backward by the tissue of the blood vessel wall, and transmit the light back to the OCT system.

As described above, when the imaging catheter emits the light to any one point on the blood vessel wall, the OCT system may acquire, at once, information in a depth direction of the blood vessel wall (from the light scattered backward), thereby enabling tomography.

In this case, the imaging catheter acquires one cross-sectional image of a blood vessel while rotating once during the process of emitting the light to the blood vessel wall and receiving the light scattered backward. In this case, the imaging catheter needs to move in equilibrium while rotating in order to acquire a three-dimensional image of the blood vessel wall.

A rotary junction and a pull-back stage are required to implement the rotation and equilibrium movement of the imaging catheter. In this case, the imaging means a process of irradiating the blood vessel wall with light, receiving light scattered backward from the tissue of the blood vessel wall, and detecting an interference signal.

As described above, the optical rotary junction module 100 for an OCT system according to the present invention is disposed between the OCT system and the imaging catheter and configured to transmit an optical signal, which is received from the OCT system, to the imaging catheter inserted into a blood vessel of a human body, and the optical rotary junction module 100 rotates the imaging catheter. The optical rotary junction module 100 for an OCT system according to the present invention will be described more specifically.

FIG. 1 is a perspective view of an optical rotary junction module for an OCT system according to a first embodiment of the present invention.

Figure 2:
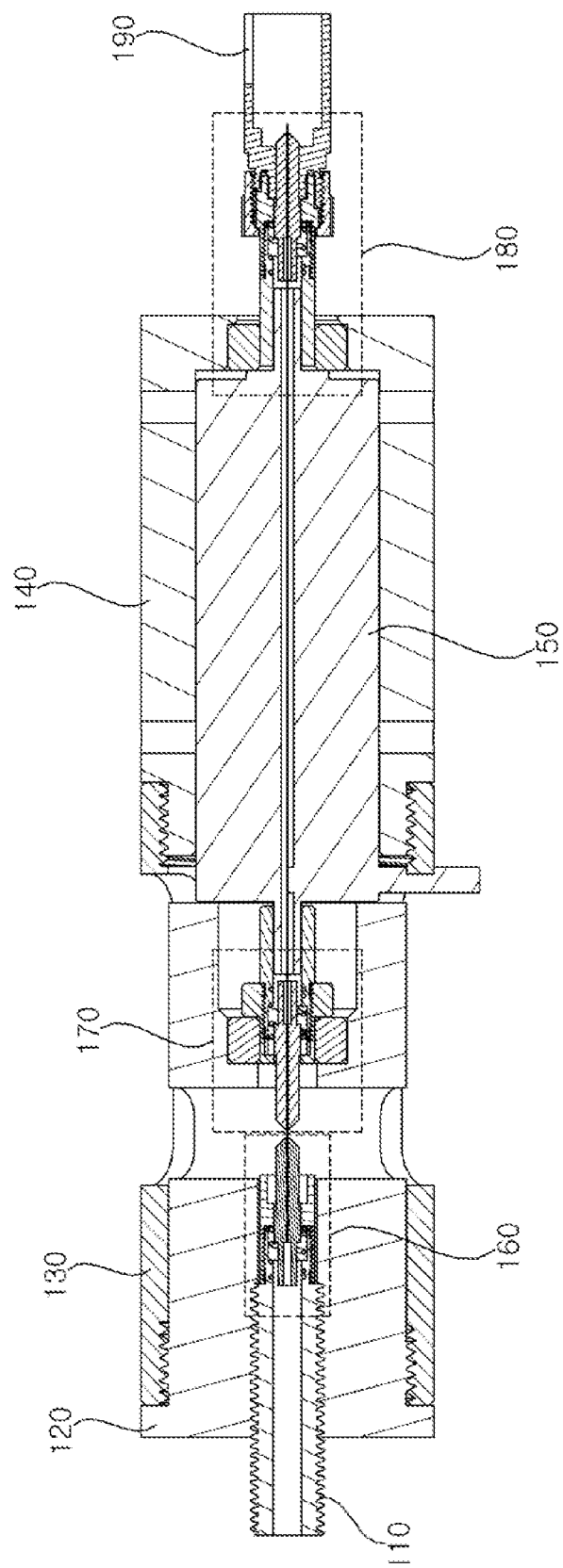
FIG. 2 is a cross-sectional view of the optical rotary junction module for an OCT system according to the first embodiment of the present invention.

As illustrated in FIGS. 1 and 2, the optical rotary junction module 100 for an OCT system according to the first embodiment of the present invention includes an OCT connection part 110, a connecting/fixing part 120, a first housing 130, a second housing 140, a hollow motor 150, a first alignment part 160, a second alignment part 170, a third alignment part 180, and an adapter 190.

Coupling structures between the above-mentioned components will be described in more detail with reference to FIG. 2 which is a cross-sectional view of the optical rotary junction module for an OCT system according to the first embodiment of the present invention.

The OCT connection part 110 is connected to the OCT system, and an optical fiber configured to transmit light, which is received from the OCT system, to the tissue of the blood vessel wall penetrates a hollow portion of the OCT connection part 110.

Figure 3:
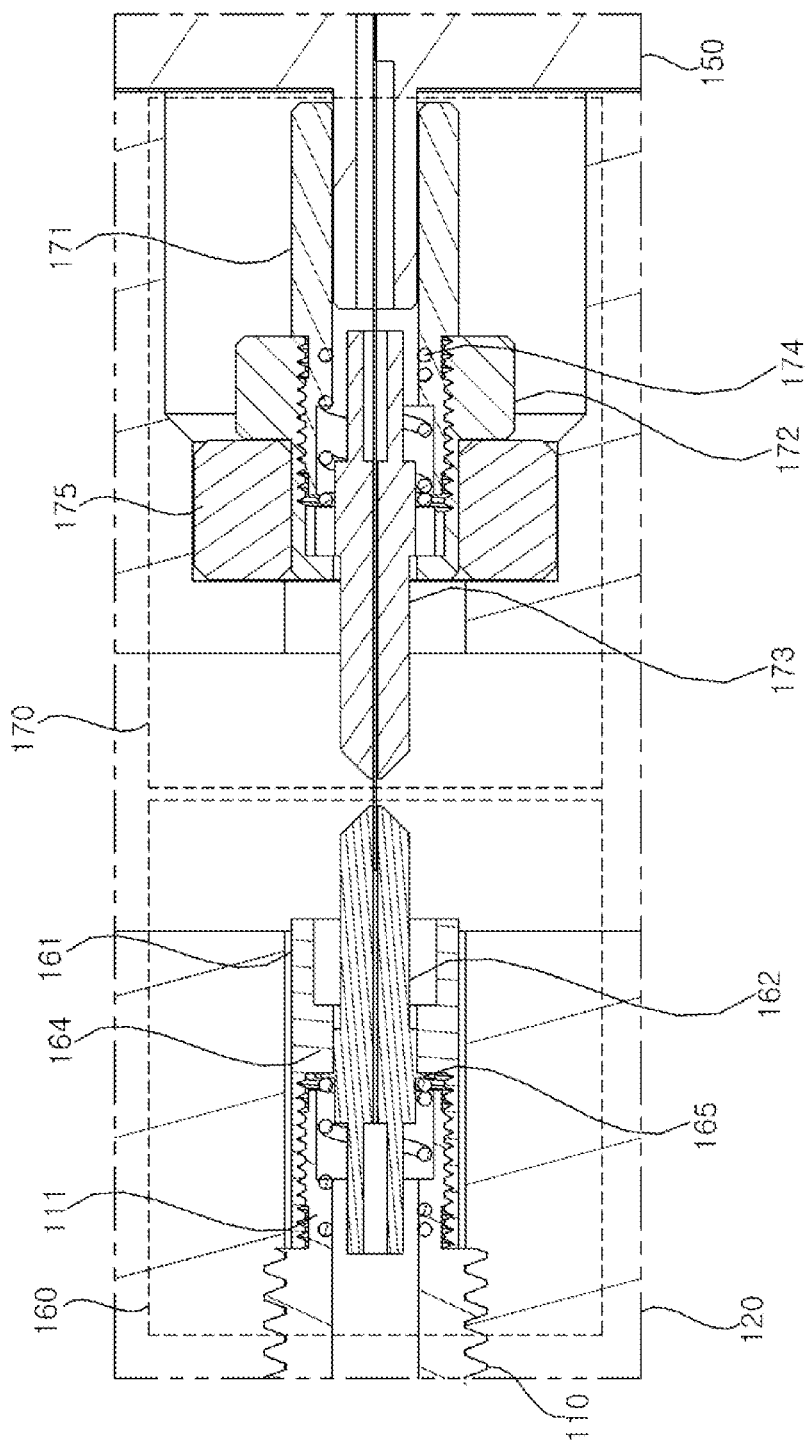
FIG. 3 is an enlarged view of a main part of the optical rotary junction module for an OCT system according to the first embodiment of the present invention.

In addition, the OCT connection part 110 has the hollow portion formed at a center thereof, and a screw thread is formed on an outer peripheral surface of the OCT connection part 110. The other end of the OCT connection part 110 opposite to one end of the OCT connection part 110 connected to the OCT system is stepped. As illustrated in FIG. 3, the OCT connection part 110 includes a stepped portion 111 having a screw thread formed on an outer peripheral surface thereof.

The connecting/fixing part 120 has a hollow portion formed at a center thereof, and a screw thread is formed on an inner peripheral surface of the hollow portion and screw-coupled to and engages with the screw thread formed on the outer peripheral surface of the OCT connection part 110, such that the OCT connection part 110 is fixed.

In addition, a screw thread is formed on an outer peripheral surface of one end of the connecting/fixing part 120, such that the connecting/fixing part 120 is also screw-coupled to the first housing 130.

The first housing 130 has a hollow portion formed at a center thereof, and screw threads are respectively formed on an inner peripheral surface of one end and an inner peripheral surface of the other end of the first housing 130. The connecting/fixing part 120 having the screw thread formed on the outer peripheral surface thereof is coupled to the inner peripheral surface of the one end of the first housing 130. The inner peripheral surface of the other end of the first housing 130 is coupled to the screw thread formed on the outer peripheral surface of the second housing 140.

The second housing 140 has a screw thread formed on an outer peripheral surface of one end thereof and coupled to the screw thread formed on the inner peripheral surface of the other end of the first housing 130. The second housing 140 has a hollow portion 141 formed at a center of thereof, and the hollow motor 150 is inserted into the hollow portion 141.

A brushless direct current motor (BLDC) may be applied as the hollow motor 150. In this case, a gear may be used to transmit power of the hollow motor, or a timing belt may be applied for a high-speed rotation.

Meanwhile, the first and second alignment parts 160 and 170 are provided in the first housing 130, more accurately, in the connecting/fixing part 120 so that the optical fiber configured to transmit the light received from the OCT system may be aligned.

Hereinafter, the first and second alignment parts 160 and 170 will be described in more detail with reference to FIG. 3 which is an enlarged view of a main part.

The first alignment part 160 includes a first ferrule fixing unit 161, a first ferrule 162, and a first spring 163.

The first ferrule fixing unit 161 has a hollow formed therein, and a screw thread is formed on a part of an inner peripheral surface of the first ferrule fixing unit 161 and coupled to the other end of the OCT connection part 110. The first ferrule fixing unit 161 is screw-coupled to the stepped portion 111 having the screw thread formed on the outer peripheral surface thereof.

The position of the optical fiber in the first ferrule 162 may be adjusted forward or rearward as the OCT connection part 110 is moved forward or rearward by adjusting the screw thread of the OCT connection part 110, i.e., the screw thread formed on the outer peripheral surface of the OCT connection part 110.

In addition, a catching projection 164 is formed on an inner peripheral surface of the first ferrule fixing unit 161, and the catching projection 164 is a portion where an inner diameter of the inner peripheral surface of the first ferrule fixing unit 161 is reduced.

The first ferrule 162 has a hollow portion formed at a center thereof so that the optical fiber in the form of a fine wire may penetrate the hollow portion of the first ferrule 162. The first ferrule 162 is inserted into and fixed to the first ferrule fixing unit 161.

Meanwhile, a catching plate 165 is formed on an outer peripheral surface of the first ferrule 162, and the catching plate 165 is fixed by being caught by the catching projection 164 when the first ferrule 162 is inserted into the first ferrule fixing unit 161.

The first spring 163 is interposed between the first ferrule 162 and the interior of the stepped portion 111 of the OCT connection part 110 and compresses the first ferrule 162, thereby enhancing the coupling between the first ferrule 162 and the first ferrule fixing unit 161.

The second alignment part 170 includes a first hollow motor connection unit 171, a second ferrule fixing unit 172, a second ferrule 173, and a second spring 174.

The first hollow motor connection unit 171 is connected to a rotary shaft of one side of the hollow motor 150 to receive a rotational force from the hollow motor 150.

The second ferrule fixing unit 172 has a screw thread formed on an inner peripheral surface thereof and is screw-coupled to the first hollow motor connection unit 171 having a screw thread formed on an outer peripheral surface thereof.

A first bearing 175 is interposed between the second ferrule fixing unit 172 and the connecting/fixing part 120 so that the rotation made by the hollow motor 150 may be smoothly performed.

The second ferrule 173 has a hollow portion formed at a center thereof so that the optical fiber, which is provided in the form of a fine wire and extends from a distal end of the first ferrule 162 of the first alignment part 160, may penetrate the hollow portion of the second ferrule 173. The second ferrule 173 is inserted into and fixed to the second ferrule fixing unit 172.

The second spring 174 is interposed between the second ferrule 173 and the interior of the first hollow motor connection unit 171 and compresses the second ferrule 173, thereby enhancing the coupling between the second ferrule 173 and the second ferrule fixing unit 172.

Meanwhile, a refractive index matching gel may be interposed between the optical fiber at the side of the first ferrule 162 of the first alignment part 160 and the optical fiber at the side of the second ferrule 173 of the second alignment part 170, thereby reducing the reflectance that occurs because of a difference in refractive index between the optical fiber and an air medium.

In addition to the method using the refractive index matching gel interposed between the optical fibers, the structure using a gradient index (GRIN) lens, which uses an alignment method in the related art, may also be used to reduce the reflectance.

Further, a third alignment part 180 configured to align the optical fiber is also provided outside one side of the second housing 140 at which the adapter 190 connecting the imaging catheter is provided, such that the light received from the OCT system is transmitted without a loss.

The optical fiber aligned by the second alignment part 170 passes through the hollow motor 150 and then is aligned once more by the third alignment part 180. The third alignment part 180 is illustrated in FIG. 4.

Figure 4:
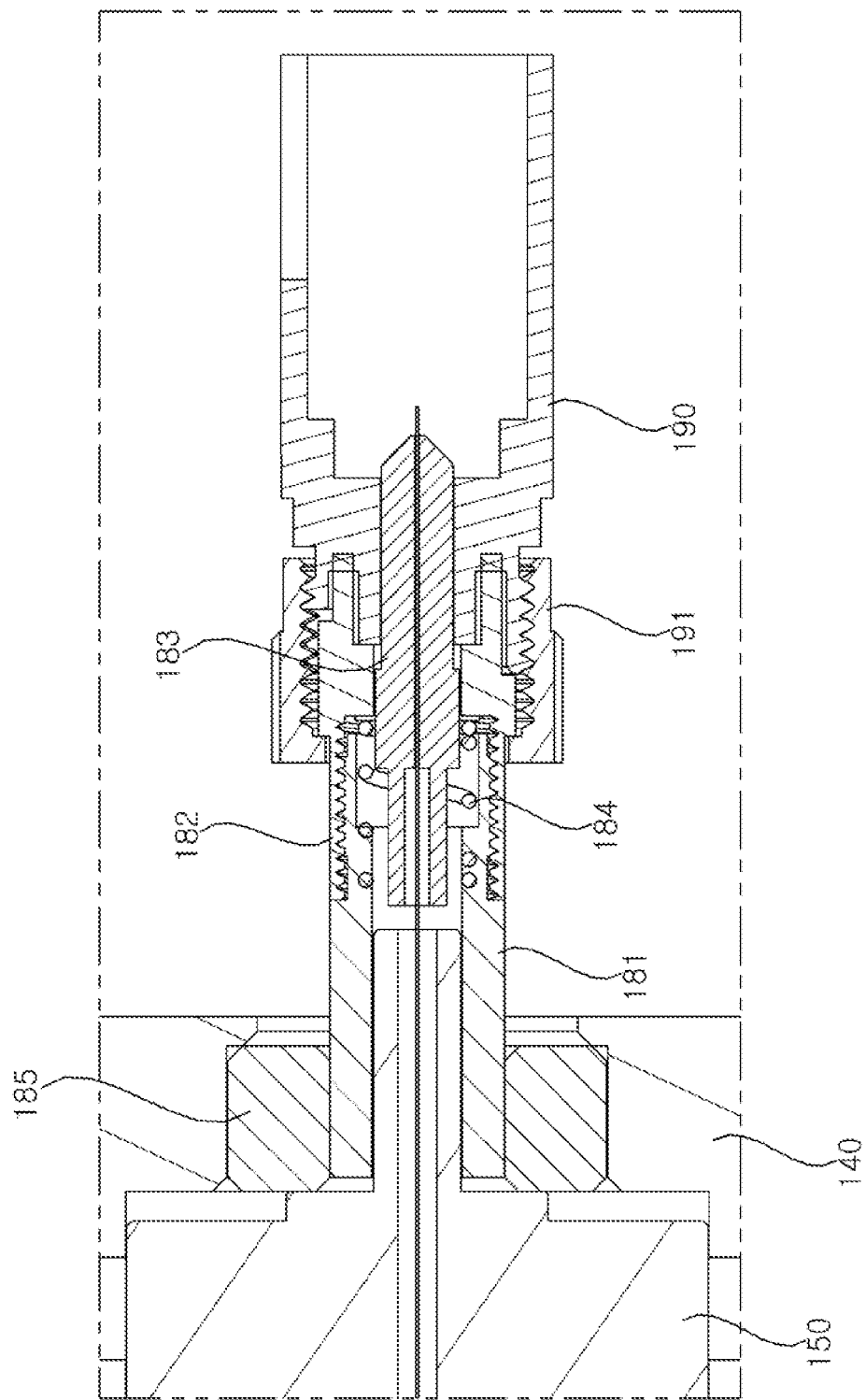
FIGS. 4 and 5 are enlarged views of another main part of the optical rotary junction module for an OCT system according to the first embodiment of the present invention.

FIG. 4 is an enlarged view of the third alignment part according to the embodiment of the optical rotary junction module for an OCT system according to the first embodiment of the present invention.

The third alignment part 180 disposed between the hollow motor 150 and the adapter 190 includes a second hollow motor connection unit 181, a third ferrule fixing unit 182, a third ferrule 183, and a third spring 184.

The second hollow motor connection unit 181 is connected to a rotary shaft of the other side of the hollow motor 150 to receive the rotational force from the hollow motor 150.

The third ferrule fixing unit 182 has a screw thread formed on an inner peripheral surface thereof and is screw-coupled to the second hollow motor connection unit 181 having a screw thread formed on an outer peripheral surface thereof.

A second bearing 185 is interposed between the third ferrule fixing unit 182 and the second housing 140 so that the rotation made by the hollow motor 150 may be smoothly performed.

The third ferrule 183 has a hollow portion formed at a center thereof so that the optical fiber having passed through the hollow motor 150 may penetrate the hollow portion of the third ferrule 183. The third ferrule 183 is inserted into and fixed to the third ferrule fixing unit 182.

The third spring 174 is interposed between the second ferrule 173 and the interior of the first hollow motor connection unit 171 and compresses the second ferrule 173, thereby enhancing the coupling between the second ferrule 173 and the second ferrule fixing unit 172.

The adapter 190 is provided so that a cap of the imaging catheter is fastened and fixed to the adapter 190. The adapter 190 is coupled to the third ferrule fixing unit 182 by means of an adapter holder 191.

Figure 5:
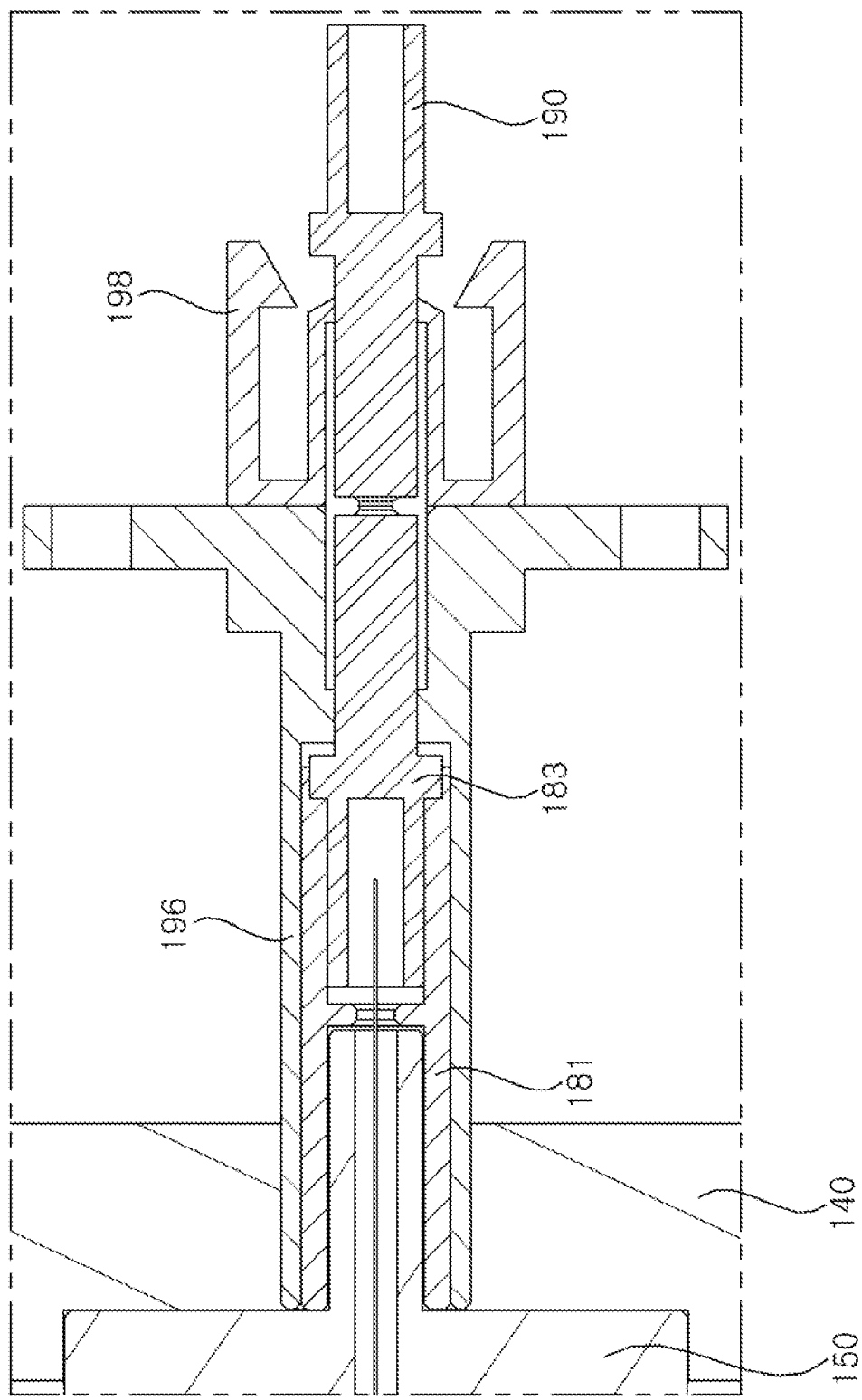

FIG. 5 is an enlarged view of the third alignment part according to another embodiment of the optical rotary junction module for an OCT system according to the first embodiment of the present invention.

The third alignment part 180 disposed between the hollow motor 150 and the adapter 190 includes the second hollow motor connection unit 181, the third ferrule 183, a T-shaped adapter 196, and an SC adapter 198.

The second hollow motor connection unit 181 is connected to the rotary shaft of the other side of the hollow motor 150 to receive the rotational force from the hollow motor 150.

The third ferrule 183 has a hollow portion formed at a center thereof so that the optical fiber having passed through the hollow motor 150 may penetrate the hollow portion of the third ferrule 183. A part of the third ferrule 183 is inserted into and fixed to the second hollow motor connection unit 181.

The second hollow motor connection unit 181 and the third ferrule 183 are inserted into and fixed to the T-shaped adapter 196.

The SC adapter 198 has a hollow portion penetrated by the adapter 190 and is coupled to the T-shaped adapter 196.

For example, after a ceramic sleeve 197 is inserted into the third ferrule 183, the SC adapter 198 may be fixed to the T-shaped adapter 196.

In addition, a material of the adapter 190 may be selected from lightweight materials capable of minimizing air resistance. In this case, the adapter 190 is provided so that the cap of the imaging catheter is fastened and fixed to the adapter 190. The adapter 190 is coupled by means of the SC adapter 198.

Figure 6:
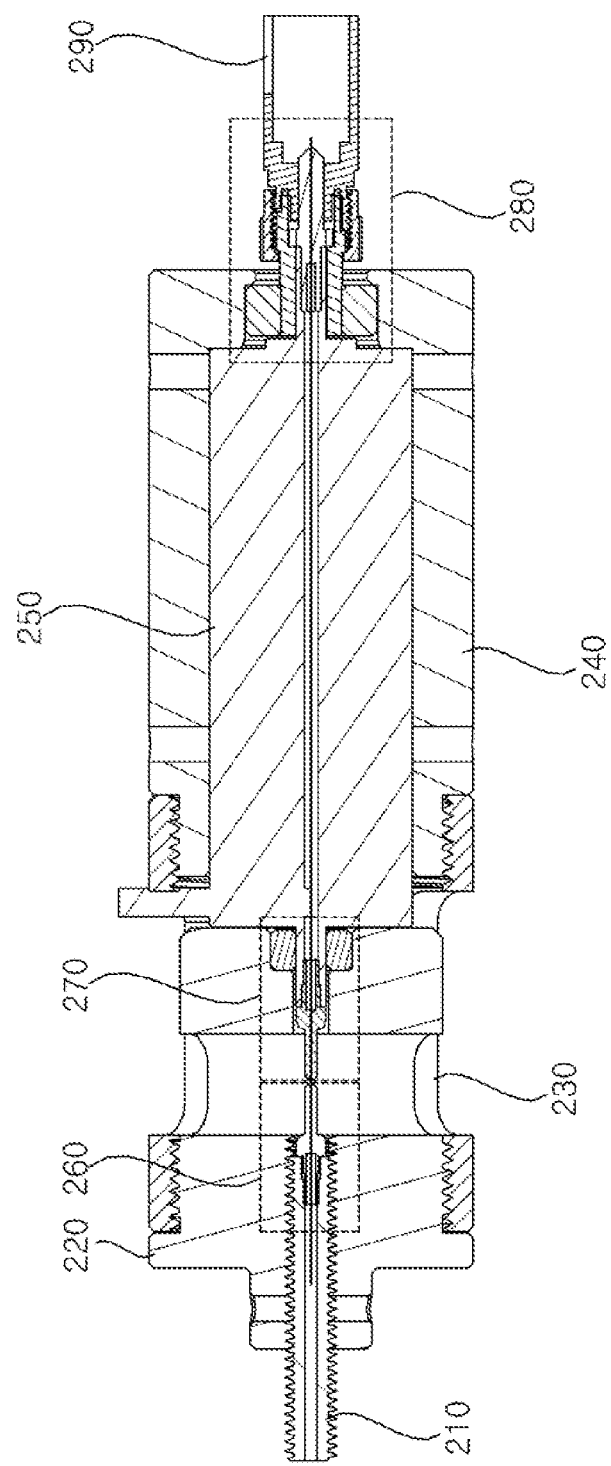
FIG. 6 is a cross-sectional view of an optical rotary junction module for an OCT system according to a second embodiment of the present invention.

FIG. 6 is a cross-sectional view of an optical rotary junction module for an OCT system according to a second embodiment of the present invention.

A rotary junction module 200 according to the second embodiment of the present invention includes an OCT connection part 210, a connecting/fixing part 220, a first housing 230, a second housing 240, a hollow motor 250, a first alignment part 260, a second alignment part 270, a third alignment part 280, and an adapter 290.

In the present embodiment, the description of the components identical to the components described in the first embodiment will be omitted, and only the components different from the components described in the first embodiment will be described.

Figure 7:
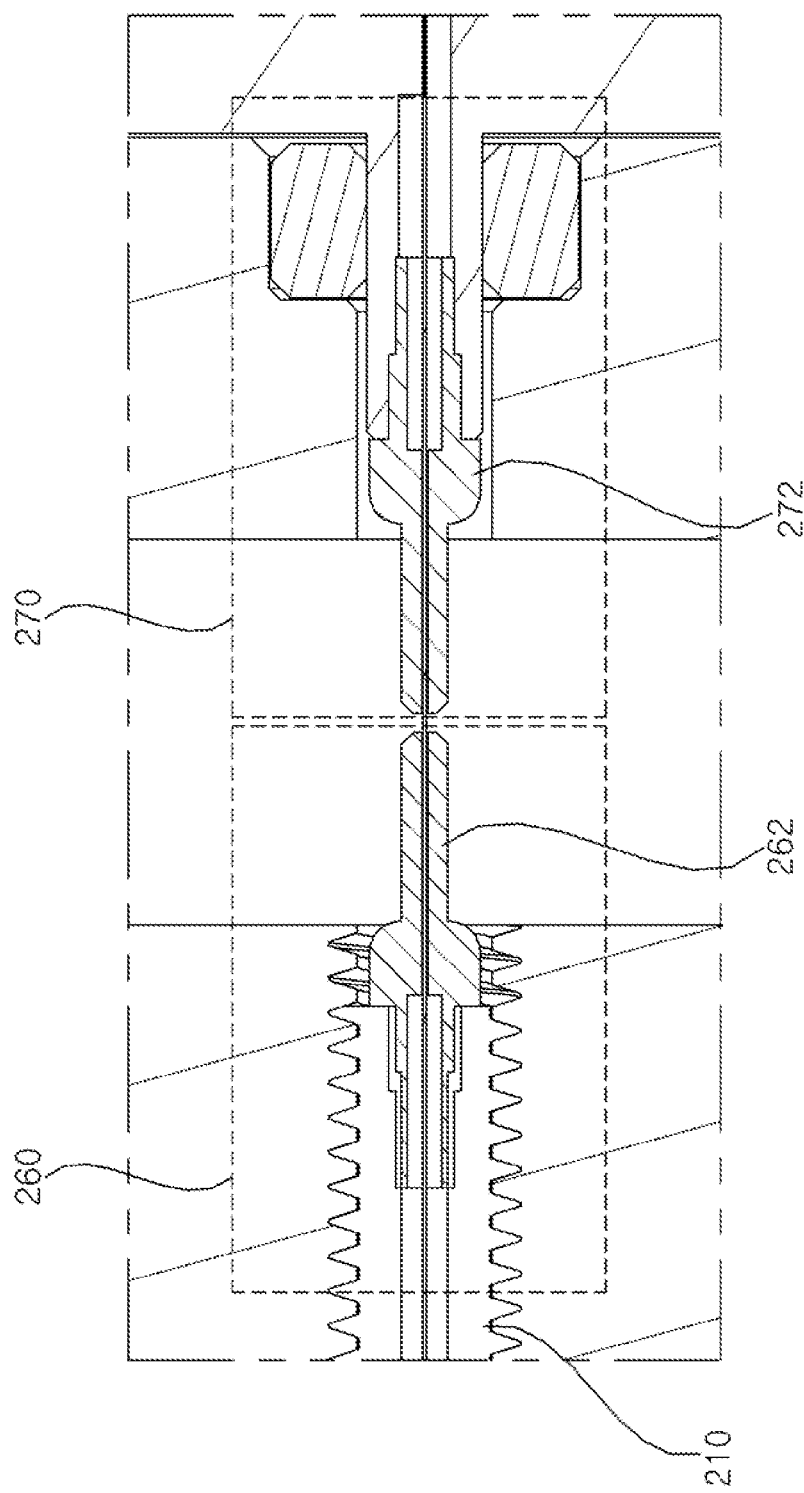
FIGS. 7 and 8 are enlarged views of a main part of the optical rotary junction module for an OCT system according to the second embodiment of the present invention.

The first and second alignment parts 260 and 270 according to the second embodiment will be described with reference to FIG. 7.

The first alignment part 260 includes a first ferrule 262. In the first embodiment, the fixing unit of the first ferrule is separately provided. However, in the present embodiment, the first ferrule 262 has one end having a stepped structure and may be fixed by being inserted into and coupled directly to the hollow portion of the OCT connection part 210 having a structure corresponding to the first ferrule 262.

The second alignment part 270 includes a second ferrule 272. Like the first ferrule 262, the second ferrule 272 has one end having a stepped structure without a fixing unit and may be fixed by being inserted into and coupled directly to the shaft of one side of the hollow motor 250 having a structure corresponding to the second ferrule 272.

Figure 8:
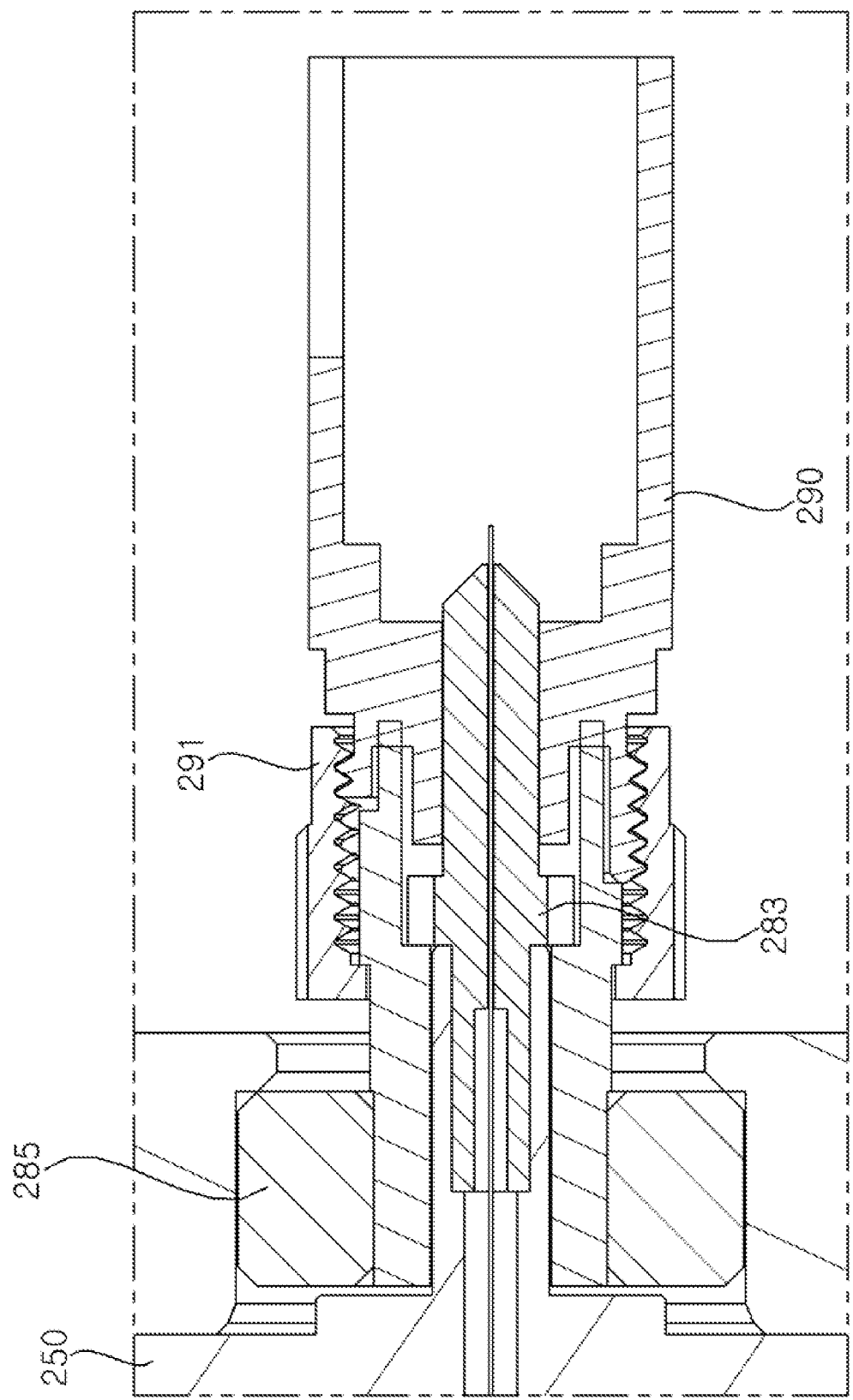

The third alignment part 280 according to the second embodiment will be described with reference to FIG. 8.

The third alignment part 280 includes a third ferrule 283. The third ferrule 283 disposed between the hollow motor 250 and the adapter 290 may be fixed by being inserted into and fixed to the shaft of the hollow motor 250.

The above description is simply given for illustratively describing the technical spirit of the present invention, and those skilled in the art to which the present invention pertains will appreciate that various changes and modifications are possible without departing from the essential characteristic of the present invention. Therefore, the exemplary embodiments disclosed in the present invention are provided for illustrative purposes only but not intended to limit the technical spirit of the present invention. The scope of the technical spirit of the present invention is not limited thereby. The protective scope of the present invention should be construed based on the following claims, and all the technical spirit in the equivalent scope thereto should be construed as falling within the scope of the present invention.

The invention claimed is:

1. An optical rotary junction module for an OCT system, the optical rotary junction module comprising:
   an OCT connection part having a screw thread formed on an outer peripheral surface thereof, the OCT connection part being connected to an OCT system configured to produce light;
   a connecting/fixing part having a screw thread formed on an inner peripheral surface thereof and screw-coupled to and engaging with the screw thread formed on the outer peripheral surface of the OCT connection part;
   a first housing having a screw thread formed on an inner peripheral surface of one end thereof and a screw thread formed on an inner peripheral surface of the other end thereof, the first housing having one end screw-coupled to the connecting/fixing part;
   a second housing screw-coupled to the screw thread formed on the inner peripheral surface of the other end of the first housing;
   a hollow motor inserted into the second housing and configured to generate rotational power;
   an adapter configured to be coupled to an imaging catheter configured to be inserted into a blood vessel of a human body and transmit light received from the OCT system;
   first and second alignment parts provided in the connecting/fixing part and configured to align an optical fiber configured to transmit the light; and
   a third alignment part disposed between the hollow motor and the adapter,
   wherein the first alignment part comprises:
   a first ferrule fixing unit having a screw thread formed on a part of an inner peripheral surface thereof and coupled to a stepped portion of the OCT connection part; and
   a first ferrule having a hollow portion so that the optical fiber penetrates the hollow portion, the first ferrule being inserted into and fixed to the first ferrule fixing unit.

2. The optical rotary junction module of claim 1, wherein the first alignment part further comprises
   a first spring interposed between the first ferrule and an interior of the stepped portion.

3. The optical rotary junction module of claim 2, wherein the second alignment part comprises:
   a first hollow motor connection unit connected to a rotary shaft of one side of the hollow motor;
   a second ferrule fixing unit having a screw thread formed on an inner peripheral surface thereof and coupled to a screw thread formed on an outer peripheral surface of the first hollow motor connection unit;

a second ferrule having a hollow portion so that the optical fiber having passed through the first alignment part penetrates the hollow portion, the second ferrule being inserted into and fixed to the second ferrule fixing unit; and a second spring interposed between the second ferrule and an interior of the first hollow motor connection unit.

4. The optical rotary junction module of claim 3, wherein the third alignment part comprises:

a second hollow motor connection unit connected to a rotary shaft of the other side of the hollow motor;

a third ferrule fixing unit having a screw thread formed on an inner peripheral surface thereof and coupled to a screw thread formed on an outer peripheral surface of the second hollow motor connection unit;

a third ferrule having a hollow portion so that the optical fiber having passed through the hollow motor penetrates the hollow portion, the third ferrule being inserted into and fixed to the third ferrule fixing unit; and a third spring interposed between the second ferrule and an interior of the second hollow motor connection unit.

5. The optical rotary junction module of claim 3, wherein the third alignment part comprises:

a second hollow motor connection unit connected to a rotary shaft of the other side of the hollow motor;

a third ferrule having a hollow portion so that the optical fiber having passed through the hollow motor penetrates the hollow portion, the third ferrule being partially inserted into the second hollow motor connection unit;

a T-shaped adapter configured such that the second hollow motor connection unit and the third ferrule are inserted into and fixed to the T-shaped adapter; and an SC adapter coupled to the T-shaped adapter and having a hollow portion penetrated by the adapter.

6. An optical rotary junction module for an OCT system, the optical rotary junction module comprising:

an OCT connection part having a screw thread formed on an outer peripheral surface thereof, the OCT connection part being connected to an OCT system configured to produce light;

a connecting/fixing part having a screw thread formed on an inner peripheral surface thereof and screw-coupled to and engaging with the screw thread formed on the outer peripheral surface of the OCT connection part;

first and second alignment parts provided in the connecting/fixing part and configured to align an optical fiber configured to transmit the light;

a first housing having a screw thread formed on an inner peripheral surface of one end thereof and a screw thread formed on an inner peripheral surface of the other end thereof, the first housing having one end screw-coupled to the connecting/fixing part;

a second housing screw-coupled to the screw thread formed on the inner peripheral surface of the other end of the first housing;

a hollow motor inserted into the second housing and configured to generate rotational power;

an adapter configured to be coupled to an imaging catheter configured to be inserted into a blood vessel of a human body and transmit light received from the OCT system; and a third alignment part disposed between the hollow motor and the adapter, wherein the first alignment part comprises a first ferrule having a hollow penetrated by the optical fiber, and the first ferrule has one end having a stepped structure and is inserted into and coupled to a hollow portion of the OCT connection part having a structure corresponding to the first ferrule.

7. The optical rotary junction module of claim 6, wherein the second alignment part comprises a second ferrule having a hollow portion so that the optical fiber having passed through the first alignment part penetrates the hollow portion, and the second ferrule has one end having a stepped structure and is inserted into and coupled directly to a shaft of one side of the hollow motor having a structure corresponding to the second ferrule.

8. The optical rotary junction module of claim 7, wherein the third alignment part comprises a third ferrule having a hollow portion so that the optical fiber having passed through the hollow motor penetrates the hollow portion, and the third ferrule is inserted into and fixed directly to a shaft of the other side of the hollow motor.

* * * * *